Figure 1:
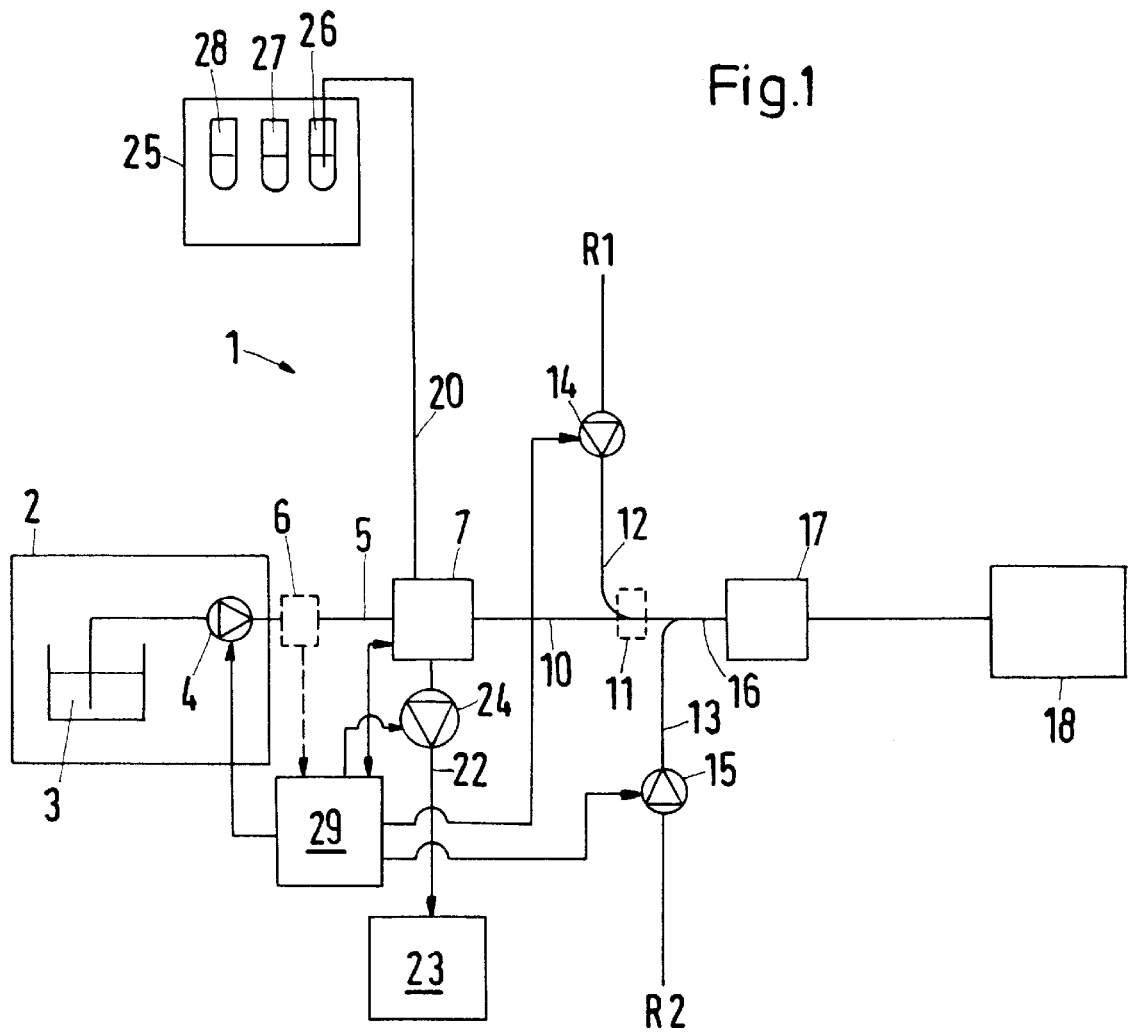

United States Patent

Karlberg et al.

[11] Patent Number: 5,869,773
[45] Date of Patent: Feb. 9, 1999

[54] ANALYSIS APPARATUS

[75] Inventors: Bo Karlberg, Sollentuna, Sweden; Ole Ploug, Allerød, Denmark

[73] Assignee: Danfoss A/S, Nordborg, Denmark

[21] Appl. No.: 850,056

[22] Filed: May 2, 1997

Related U.S. Application Data

[62] Division of Ser. No. 718,480, Nov. 21, 1996.

[30] Foreign Application Priority Data

Mar. 31, 1994 [DE] Germany ............ 44 11 266.1

[51] Int. Cl.$^6$ .................................................. G01N 33/00
[52] U.S. Cl. .................. 73/863.01; 422/82; 73/864.81
[58] Field of Search ................ 73/23.41, 23.42, 73/61.55, 61.56, 64.56, 863.72, 863.73, 863.83, 864.34, 864.81, 864.83, 864.84; 422/81, 82

[56] References Cited

U.S. PATENT DOCUMENTS 4,486,097  12/1984  Riley ........................................ 356/410
4,908,187  3/1990  Holmquist et al. ........................ 422/81

*Primary Examiner*—Robert Raevis
*Attorney, Agent, or Firm*—Lee, Mann, Smith, McWilliams, Sweeney & Ohlson

[57] ABSTRACT

An analysis method is disclosed, in which several samples are passed in succession through a reaction channel to a detector (17), and at least one reagent is introduced into the reaction channel (16) for reaction with the samples. An apparatus for implementing the method is also disclosed. Using the method and the apparatus, it is intended to specify an analysis method more capable of coping with different flow characteristics of the samples in fluid form. For that purpose, each sample and its associated reagent is introduced in a controlled manner into the reaction channel so that they form a block, along the length of which the local volume ratio between sample and reagent, averaged over a segment of predetermined length, is substantially constant, the length of the segment being substantially shorter than half the length of the block.

4 Claims, 3 Drawing Sheets

ANALYSIS APPARATUS

This application is a division of Ser. No. 718,480 filed Nov. 21, 1996.

The invention relates to an analysis apparatus having a sample feed duct, at least one reagent feed duct, a pumping device for sample and reagent, and a reaction channel and a detector.

There is a constantly growing need for chemical analysis in many areas. The area of environmental protection can be quoted as an example. Here, for example, when bodies of water are being monitored, water samples have to be removed continuously from the body of water and examined for contaminants. The operation of sewage treatment plants, for example, the injection of air, is effected in dependence on specific substances contained in the water to be purified. Such analyses have to be performed at frequent intervals, with the result that not only is the number of analyses large, but the analyses also have to be carried out as quickly as possible. The same applies to the disciplines of medicine and environmental analysis. In large laboratories, as a rule very many samples have to be examined. This can no longer be carried out using conventional manual methods, in which the sample to be examined is mixed with reagents, for example, in a beaker, and a resulting reaction product is recorded and evaluated for type and quantity. An additional complicating factor is that normally it is not just a single reaction step that has to be carried out but a number of reaction steps. This not only requires manpower, but also the provision of correspondingly large laboratory areas in which the samples to which reagents have been added can be stored in the interim until they have reacted and/or until the reaction product has been evaluated. Moreover, relatively large amounts of samples and reagents are necessary for the manual methods, which renders waste management difficult.

For those reasons, a start was made some decades ago on the development of continuous or semi-continuous methods which could function with smaller sample sizes and with fewer reagents. Because these methods have been "mechanized" it is also possible to examine a larger number of samples in the same time. The methodology has been retained here, that is to say, the sample is mixed with one or more reagents and the resulting reaction product is detected using a detector.

U.S. Pat. No. 2,797,149 and U.S. Pat. No. 2,879,141 describe a so-called "Segmented Flow Analysis" (SFA), that is to say, an analysis method in which successive sample segments are separated by air bubbles in the sample duct. After mixing each sample segment with one or more reagents, the reaction product can be evaluated separately in each segment. By choosing the length of the reaction channel, the time available for the reaction can be adjusted. The use of air bubbles in the reaction channel to separate the individual samples produces a compressible fluid column, however, so that the flow speed, and thus the reaction time, cannot be accurately monitored.

U.S. Pat. No. 4,022,575 and DE 28 06 157 C2 disclose a more recent method, which is known as "Flow Injection Analysis" (FIA). Here, the individual samples are introduced at specific distances apart into a carrier fluid so that successive samples are always separated by a segment of pure carrier fluid. This carrier fluid partly charged with samples is then mixed with the reagent or reagents. Evaluation of the reaction product is effected in a similar manner by a detector, which records the reaction product according to type and/or quantity. Because the samples are diluted by the carrier fluid within a sample segment on the one hand, and because of the transition between a segment comprising a sample-carrier fluid mixture and a segment of pure carrier fluid on the other hand, which leads to further distortion of the sample concentration at the start and the end of each sample segment, in this method there is only very limited scope for waiting until a steady state obtains. The detector accordingly no longer evaluates a signal at which a constant reaction product signal is present, but a transient signal, normally in the form of a peaked signal pulse. The segments of pure carrier fluid between the individual segments of sample and carrier fluid, referred to hereinafter as "sample segments" or "sample blocks" for short, can be used to define a starting point for each measurement. However, the dilution factor, also called the "dispersion coefficient" has to be determined in a separate test. Only from comparison of the dispersion coefficient with the measurement signal obtained is it possible to determine the analysis result quantitatively. In practice therefore, a calibration with samples of known concentration preferably needs to be carried out. Moreover, differences in viscosity from sample to sample may influence the dilution effect to such an extent that measurement errors which cannot be eliminated by a calibration occur.

The invention is based on the problem of providing an analysis method more capable of coping with different flow properties of the samples.

In an analysis method of the kind mentioned in the introduction, this problem is solved in that each sample and its associated reagent is introduced in a controlled manner into the reaction channel so that they form a block, along the length of which the local volume ratio between sample and reagent, averaged over a reaction channel section of predetermined length, is substantially constant, the length of the reaction channel section being substantially shorter than half the length of the block.

The local mean volume ratio means here a volume ratio which is present in a hypothetical reaction channel section which symmetrically surrounds the site chosen for localisation. This hypothetical reaction section therefore extends from the chosen site an equal distance in the flow direction and against the flow direction. It has the said predetermined length. When determining the dimension of this length, it should be borne in mind that it is small compared to the overall length of the block. It is substantially smaller than half of that length. The volume of the reaction channel section is therefore small in relation to the overall volume of the reaction channel and likewise small in relation to the volume of the respective block. On the other hand, the length of the reaction channel section's should not be too short, since local fluctuations in the volume ratio in the region of the intake are expressly allowed. They are compensated for, however, in that intermixing by convection and by diffusion of the participant fluids, that is, the sample and the reagent, takes place in the reaction channel, likewise locally. The length of the reaction channel section in question is therefore to be selected so that averaging of the volume ratio over this reaction channel section corresponds to levelling-out the fluctuation in the volume ratio.

Controlling the introduction of sample and reagent in this manner ensures that in the particular block being conveyed to the detector there is a substantially constant component ratio between sample and reagent. Accordingly, using the reaction product it is actually possible to provide evidence of the proportion of the substance to be detected in the sample.

In a preferred embodiment, the flow rate of each block in the reaction channel is selected in dependence on the dimensions of the reaction channel and the length of the block to be so small that within each block there remains a reaction core which contains exclusively the sample an d its reagent. In this reaction core there is therefore a substantially constant distribution of the reaction product, so that the detector which records the reaction product produces a signal which persists steadily on a plateau virtually for as long as the reaction core requires to pass through the detector. This Simplifies the evaluation quite considerably. The signal can be evaluated directly, without, apart from a calibration, having to fall back on reference variables or signal gradients.

It is also preferable for an integrating measurement to be taken in the detector over a volume which is smaller than the volume of the reaction core. This embodiment on the one hand enables local fluctuations to be evened-out by integration, but on the other hand, the integration volume is small enough to ensure that errors as a result of inadvertent incorporation of adjacent samples are not allowed to occur.

The local mean volume ratio between each individual sample and its reagent is preferably substantially constant at any location of the reaction channel at any time. The initial condition prevailing only on introduction is therefore maintained throughout the reaction channel, for example, by appropriate flow control.

Successive samples are preferably introduced into the reaction channel adjoining one another. In contrast to the state of the art, washing out the individual samples with a carrier fluid before the next sample is introduced is dispensed with. The washing fluid or carrier fluid involves the problem that this fluid first has to be washed out with the next sample before a measuring signal can be read out. The carrier fluid here gives rise to a relatively high dilution, the magnitude of which is also dependent on the viscosity, which can vary from sample to sample. This in turn can have adverse and unpredictable effects on the signal characteristic at the signal output of the detector. This advantageous construction frees one in principle from the implicit preconditions that were previously regarded as generally necessary by the experts. It is sufficient to wash out the previous sample with the following sample. The consumption of time and fluid is drastically reduced by this step. Moreover, analysis results of improved accuracy are also achieved, because the influence of viscosity effects is reduced.

Preferably, volumes of sample and reagent, each determined in advance, are fed with great accuracy into the reaction channel. This great accuracy of the infeed, that is, adherence to specific volumes and/or flow rates, cannot normally be achieved with the peristaltic pumps known from U.S. Pat. No. 2,797,149 and DE 28 06 157 C2. These peristaltic pumps normally have at least one resilient hose which is subjected to recurring deformation. It is virtually inevitable that this deformation will lead in the long run to a change in the delivery volumes. This change cannot be predicted, however, so that even with an initially relatively accurate pumping, it is impossible to ensure that pumping of sample and reagent will be effected in the respective volumes determined in advance. The relatively accurate pumping, that is, matching of the flow rates of sample and reagent, therefore enables exact predeterminable volume ratios of sample and reagent to be set. The accurate infeed also enables an improved consistency of the reaction procedures to be achieved, so that the existing mechanized method is able to operate with virtually the same accuracy as the conventional, manually performed methods.

In a preferred construction of the invention, provision is made for sample and reagent to be introduced in layers into the reaction channel. The term "in layers" refers only to the instant of introduction, however. As a laminar flow develops, one can observe that a mutual diffusion of sample and reagent is effected at the interface or area of contact between sample and reagent. The "layers" of sample and reagent can therefore no longer be exactly separated a certain time after introduction. Nevertheless, at least in theory it is possible to imagine such a layering at the instant of introduction. The two fluids of the sample and reagent are, as it were, placed one against the another. This arrangement simplifies intermixing of sample and reagent in the region of laminar flow. The desired reaction time can be achieved by a suitably slow advancement of sample and reagent through the reaction channel. Mutual intermixing of sample and reagent can here be attributed partly to diffusion. In a reaction channel which changes direction, however, transversal regions of flow also occur, which lead to increased intermixing of the fluid by convection.

In an especially preferred construction, provision is made for more than two layers to be produced during infeed, adjacent layers being formed by sample and reagent respectively. The interface between sample and reagent is thereby enlarged. If, for example, instead of two layers comprising sample and reagent, three layers thereof are used, which form a sandwich-like construction on the basis of the requirement that adjacent layers are formed by sample and reagent respectively, the interface is doubled. The time required for intermixing decreases correspondingly.

Sample and reagent are preferably fed into the reaction channel parallel to one another in the flow direction. In that case, there is a relatively large interface which extends along the axis of the reaction channel. There is therefore a sufficiently large interface available for mutual diffusion of sample and reagent. Exchange between sample and reagent is maintained until the individual concentrations have equalized. This exchange is not dependent on whether the block formed by sample and reagent is moving through the reaction channel or not.

It is here especially preferred for the admission of sample and reagent to be effected synchronously with respect to one another. Such a synchronous admission can be achieved, for example, by synchronously controlled pumps, for example, by synchronously operated piston pumps. In such a construction, the two fluids comprising sample and reagent are, as it were, positioned side by side.

In an alternative construction, sample and reagent can be fed alternately in succession and adjoining one another into the reaction channel, the length of the individual sample and reagent segments being substantially shorter than the length of the block. Although only the cross-sectional area of the reaction channel is available as exchange area, that is, the area which is also available for the flow through, the individual segments of sample and reagent are here kept relatively short, so that within a single sample-reagent block formed from a plurality of such segments a relatively large interface is accordingly produced. Intermixing is then effected axially, that is to say, in the flow direction.

Preferably, an overall volume of sample and reagent corresponding at least to three times the volume of the reaction channel is fed into the reaction channel. With such a large volume, one can ensure that traces of previous blocks, that is, of previous samples, have been removed completely from the reaction channel. Despite the triple overall volume, the consumption of chemicals remains relatively small owing to the construction of the apparatus and its miniaturization.

Advantageously, detection of the reaction product is effected as the middle third of the overall volume is flowing through. During that period, it is not only possible to ensure with a relatively high degree of probability that preceding samples no longer have any influence on the reaction product of the sample undergoing investigation at that moment, it is also possible to avoid a subsequent sample having any effect on the reaction product.

The sample is preferably formed by a fluid that passes along one side of a membrane, the other side of the membrane being exposed to a medium which contains the constituent to be detected. In particular when analyzing sewage, this eliminates mechanical removal of the sewage for the purpose of introducing it into the reaction channel. On the contrary, the constituent to be analyzed, that is, for example, a salt, phosphate, nitrate or similar substance, is transported through the membrane into the fluid. This procedure is based essentially on dialysis. The method can therefore dispense with additional mechanical working steps.

The flow rate is preferably selected so that with a given cross-sectional area of the reaction channel, a Reynolds number for sample and reagent of 5 or less is obtained. The flow rate is thus kept very low, which has the advantage that the outward bulge developing at the start of the block formed by the sample and reagent and the corresponding inward bulge at the end of the block remain relatively small. Accordingly, axial intermixing of successive blocks is kept to a minimum, so that relatively short blocks can be used without fear that successive samples will adversely affect each other. The volume of the sample, and accordingly the volumes of the reagents used, can thus be kept small whilst maintaining the quality of the measurement. The slow flow rate also enables the length of the reaction channel to be kept correspondingly short whilst maintaining the same reaction time, so that the volume of the reaction channel overall can be kept small.

It is also preferred for the length of the individual samples to be kept so small that the analysis is effected continuously or semi-continuously. In many cases, it is sensible not just to feed individual samples in succession into the sample channel, but to send a continuous sample flow through the sample channel. It is here that the particular advantage of the inventive method, which eliminates the need to separate the individual samples from one another, is demonstrated. By controlling the feed of sample fluid and reagent fluid in such a manner that the volume ratio is constant, even with continuous feed the desired high accuracy is achieved.

With an analysis apparatus of the kind mentioned in the introduction, the problem is solved in that the pumping device for each of sample and/or reagent has a respective pump, the delivery amount of which is controllable.

The choice of pump is of a certain significance for the present invention when one wishes to obtain accurate measurement results with the method and the apparatus. In that case, by suitable control of the pumps, results that correspond to those of conventional manual analysis methods can be obtained.

Using this construction, the sample fluid and the reagent fluid can be caused to enter the reaction channel at a controllable and Consistent flow rate. By this means, a layered structure transverse to the longitudinal direction of the reaction channel is obtained. Mutual diffusion or intermixing of sample and reagent is not effected directly as the sample feed duct meets the reagent feed duct, but gradually somewhat later in the reaction channel, and then predominantly by radial diffusion or mixing. Axial mixing of successive blocks is avoided by this measure.

The pump in this case is preferably in the form of a piston pump which is driven by a d.c. motor or stepper motor. With a piston pump, the delivered volume can be matched with great accuracy to a desired requirement. Piston pumps can moreover also be controlled synchronously with great accuracy, so that pumping of sample and reagent can be correspondingly accurately and synchronously controlled.

Advantageously, the sample feed duct and the reagent feed duct are connected to two inputs of a feed valve, which connects the two feed ducts alternately to the reaction channel. In this embodiment, a layered structure is produced in the reaction channel, with the sample fluid and reagent fluid being arranged in layers immediately adjoining one another. The advancement of a block formed in this manner from sample and reagent is not necessarily effected continuously, but is optionally in steps, because pumping cannot always be guaranteed during the change-over operation of the feed valve. Nevertheless, even with this step-wise advancement of the block, satisfactory diffusion and subsequent reaction of sample and reagent is achieved.

The flow cross-section of the reaction channel preferably has a larger dimension in one direction than in the direction at right angles to this dimension. In particular when sample and reagent are fed in in parallel, this allows a larger interface to be created, which in turn promotes radial intermixing.

The flow cross-section is preferably substantially rectangular. Infeed is then effected substantially parallel to the longitudinal sides of the rectangle, so that a correspondingly large interface is available for exchange of sample and reagent.

The reaction channel preferably has a flow cross-section of 0.5 mm$^2$ or less and a length of 250 mm or less, and the pumping device generates a volume flow of 100 $\mu$l/min or less. The overall volume of the reaction channel is correspondingly small. This also means that only a very small amount of fluid is required for the analysis. The very small volume flow contributes further to keeping the consumption of chemicals very small. Nevertheless, a construction of the reaction channel of this kind enables excellent results to be achieved.

It is also preferred for the detector to have a detector volume which is smaller than the volume of the reaction core. The detector therefore integrates only over a volume in which conditions are undisturbed, that is, in which there is no influence from adjacent samples.

Figure 2:
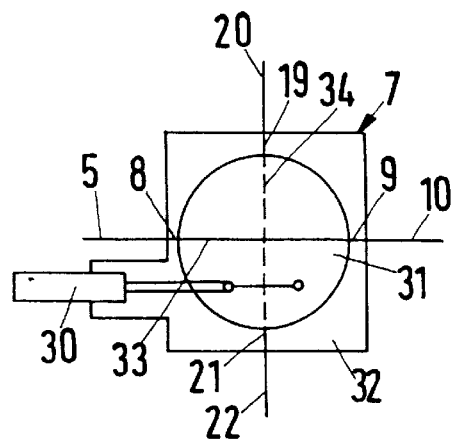
Figure 3:
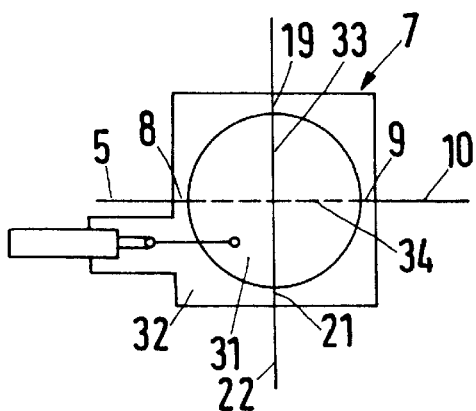
Figure 4:
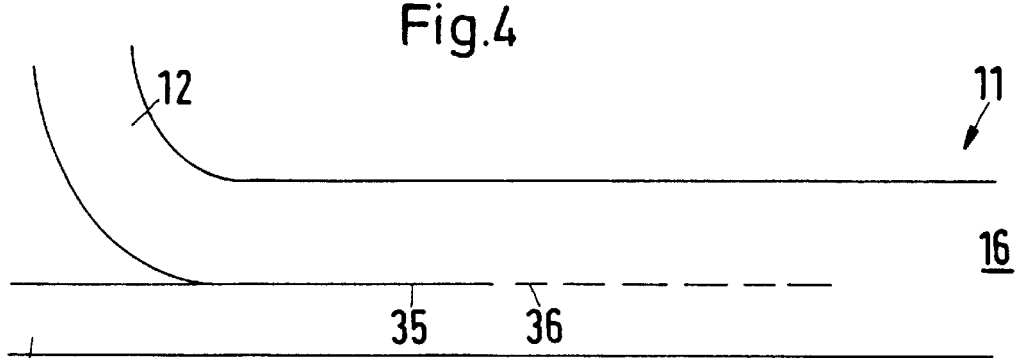
Figure 5:
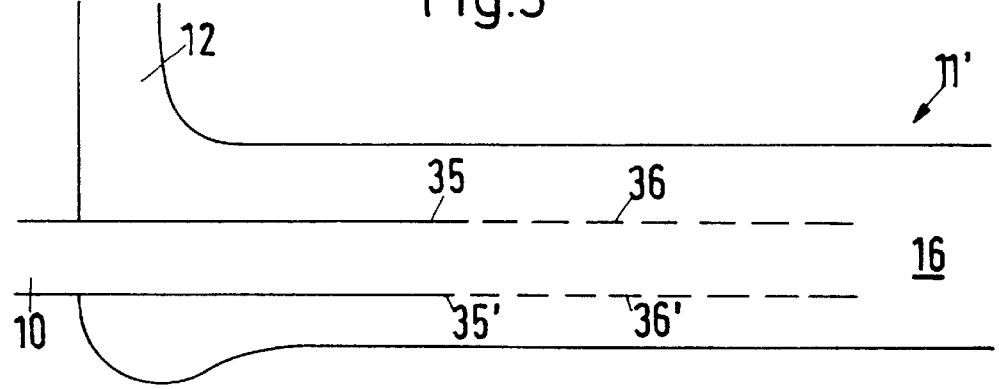
Figure 6:
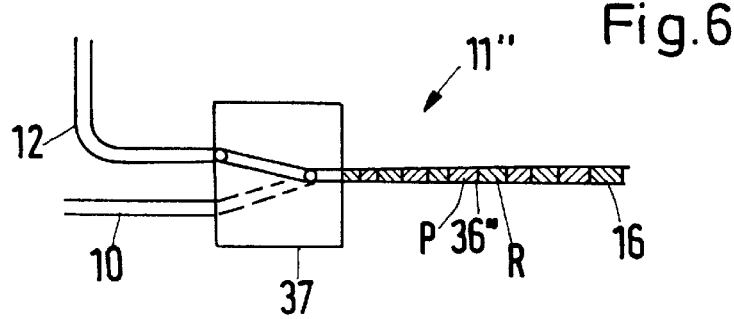
Figure 7:
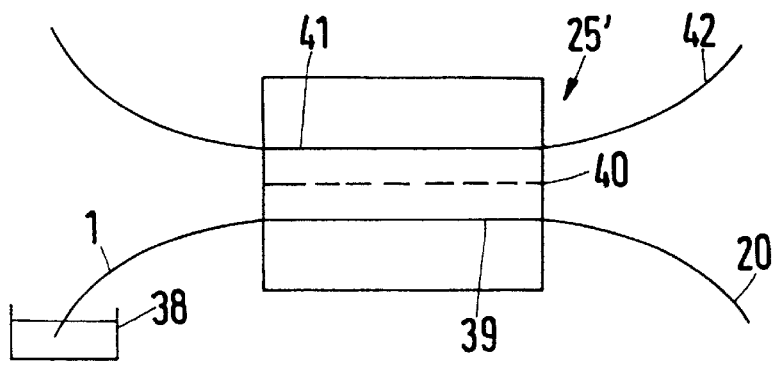
Figure 8:
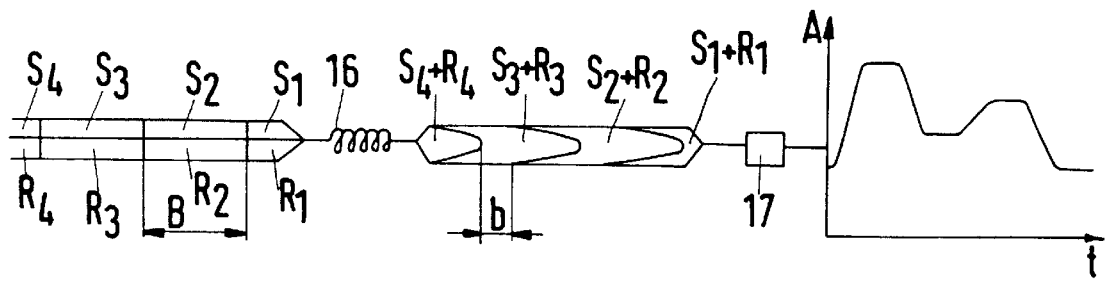
Figure 8:
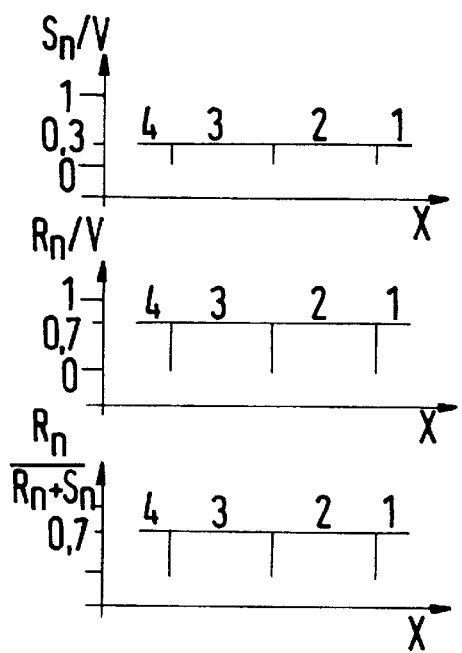
Figure 8:
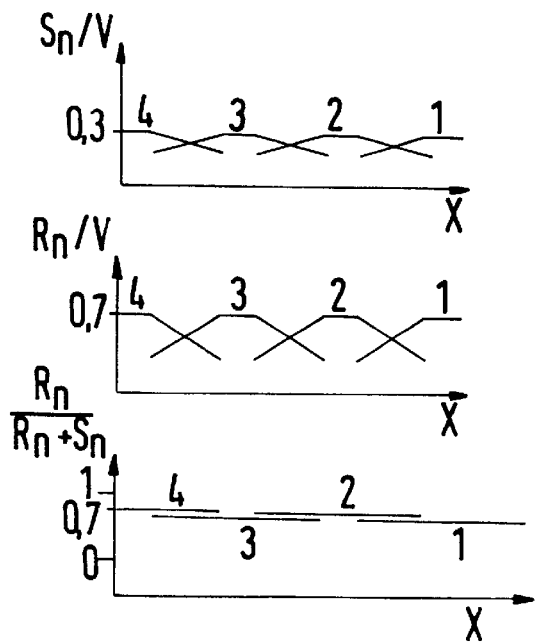

The invention is described hereinafter with reference to preferred embodiments, in conjunction with the drawing, in which FIG. 1 shows an analysis apparatus, FIG. 2 shows a change-over valve in a first position, FIG. 3 shows the change-over valve in a second position, FIG. 4 shows a first construction of a mixing point, FIG. 5 shows a second construction of a mixing point, FIG. 6 shows a third construction of a mixing point, FIG. 7 shows a device for producing a sample fluid and FIG. 8 is a diagrammatic illustration of the mixing and a signal plot.

An analysis apparatus 1 comprises a carrier fluid source 2, which in the embodiment illustrated consists of a reservoir 3 for carrier fluid and a pump 4. The carrier fluid source 2 is joined by way of a carrier fluid duct 5, in which a flowmeter 6 is optionally arranged, to a change-over valve 7, namely to its carrier input 8. The flowmeter 6 is not absolutely necessary. If required, the amount of fluid delivered can be determined from the delivery volume of the pump 4, for example, from its piston stroke. This can in turn also be ascertained or controlled indirectly, for example, by way of the driving power.

The change-over valve 7 has a sample outlet 9 which is connected to a sample duct 10. The sample duct 10 is connected in a manner known per se to one of several mixing points 11, to which reagents R1, R2 are fed by way of respective first and second reagent ducts 12, 13 in each of which a respective pump 14, 15 is arranged. A reaction channel 16, in which a detector 17 is arranged, adjoins the mixing points 11. The output of the detector 17 is connected to a waste collecting vessel 23.

The change-over valve 7 has a sample inlet 19 which is connected to a sample duct 20, which in turn is connected to a sample removal station, and a waste outlet 21, which is connected to a waste duct 22. Arranged in the waste duct 22 is a pump 24 the output of which is connected to a wast collecting vessel 23. Different samples 26–28 are held in the sample removal station ready to be sucked in succession into the change-over valve.

In addition, a control device 29 is provided, which is connected to the flowmeter 6, if this is present, and receives information from it. The control device 29 controls the pump 4 for the carrier fluid and the pump 24 in the waste duct 22. In addition, the control device 29 controls the change-over valve with the assistance of an operating device 30 in the form of a piston-cylinder arrangement. Optionally, the drive of each pump 4, 24 is coupled back to the control device.

The change-over valve 7 comprises herein a rotatable body 31 which is in the form of a stopper and is arranged rotatably in a housing 32. The rotatable body 31 has a first channel 33 and a second channel 34. In the position illustrated in FIG. 2, the first channel 33 connects the carrier inlet 8 to the sample outlet 9, whilst the second channel 34 connects the sample inlet 19 to the waste outlet 21. In the position illustrated in FIG. 3, in which the rotatable body 31 has been rotated through 90° with respect to the position in FIG. 2, the first channel 33 connects the sample inlet 19 to the waste outlet 21, whilst the second channel 34 connects the carrier inlet 8 to the sample outlet 9. The position of the rotatable body 31 can be reported to the control device 29 by way of the line illustrated in FIG. 1 by the double-ended arrow, between the change-over valve 7 and the control device 29.

In the position illustrated in FIG. 2, the pump 24 sucks a sample 26 through the sample duct 20 into the second channel 34, until this is completely full of the second sample. Whether more sample is introduced than is needed to fill the channel completely is immaterial. Complete filling of the second channel 34 with the sample 26 ought to be ensured however. On rotation of the rotatable body 31 through 90°, the second channel 34 thus filled assumes a position illustrated in FIG. 3. In this position, the second channel 34 connects the carrier inlet 8 to the sample outlet 9. The control device 29 now starts up the pump 4 for the carrier fluid. The carrier fluid which is now being transporter & enters the second channel 34 and thus forces the sample located in the second channel 34 through the sample outlet 9 into the sample duct 10. The volume of the second channel 34 (and, of course, also of the first channel 33) and the delivery volume of the pump 4 are known. The control device 29 is therefore able to stop the pump 4 for the carrier fluid and to rotate the rotatable body 31 again through 90° into the position illustrated in FIG. 2 before the carrier fluid is able to pass through the second channel 34 into the sample outlet 9.

As long as the rotatable body 31 is located in the position illustrated in FIG. 3, in which the second channel 34 is emptied under the influence of the carrier fluid into the sample outlet 9, the first channel 33 can be filled with a subsequent sample, for example, the sample 27. As the pump 24 for the sample has a larger output capacity than the pump 4 for the carrier fluid, that is to say, has a larger output capacity than the carrier fluid source 2, the channel between the sample inlet 19 and the waste outlet 9 is always completely filled before the carrier fluid enters the sample outlet 9. In this manner, waiting times are reduced. Control of the change-over valve 7 is considerably simplified.

In the sample duct 10, a column of fluid is therefore created in which one sample segment follows immediately after the next without a gap. At the mixing point 11, the reagent R1 is added. At a further mixing point, which is not separately shown, the reagent R2 is added. Further mixing points for further reagents can, of course, also be present. The reagents R1 and R2 then react in the reaction channel 16 with the samples in the individual sample segments and produce one or more reaction products which can be detected by means of the detector 17. Once it has successfully been evaluated by the detector 17, the fluid in the reaction channel 16 can be transported to the waste collecting vessel 18.

FIG. 4 shows a first construction of the mixing point 11. The term "mixing point" has been chosen here merely for reasons of simplicity. As apparent from the following, the actual mixing does not take place at this point. The sample duct 10 and the reagent duct 12 for the first reagent R1 meet at right angles to one another here. Nevertheless, with suitable flow control, the sample fluid and the reagent fluid flow into the reaction channel 16 substantially in parallel, provided that the flow rate is so low that operation takes place in the laminar region. A broken line 36, the segments of which become shorter and shorter, indicates that the layering of sample fluid and reagent fluid occurring directly at the confluence slowly disappears. After a certain length, it is impossible to detect a clear boundary between the sample fluid and the reagent fluid in the reaction channel 16. On the contrary, an increasingly enlarging zone will form along the line 36, in which sample fluid and reagent fluid mix with one another. The mixing operation is effected here initially by diffusion, that is to say, by an equalization of differences in concentration between the sample and the reagent. Since this equalization is effected in both directions, that is from the sample to the reagent and from the reagent to the sample, this provides a very good intermixing and after a certain time also a complete intermixing of sample and reagent. To reduce the mixing and reaction time, it can also be sensible to let the reaction channel change direction several times, for example, to construct it in serpentine form. Transversal flow portions then occur in each curve or corner, leading to enhanced intermixing of sample and reagent by convection.

The mixing point for the second reagent duct 13 is of the same construction. As soon as sample and reagent mix, that is, as soon as molecules from the sample fluid have entered the reagent fluid and vice versa, reactions can take place which ultimately lead to the reaction product which is to be detected with the detector 17.

FIG. 5 shows a modified embodiment of a mixing point 11', in which two reagent ducts 12 and 12' are guided in such a manner that they emerge into the reaction channel 16 on each side of the sample duct 10. Both reagent ducts 12, 12' can be fed from the same source or can even form two ends of a common feed duct. There are therefore two interfaces 36, 36'. It is obvious that the opportunity for sample and reagent to intermix is consequently much improved. The time taken to adhieve a satisfactory intermixing is reduced.

FIG. 6 shows a third embodiment of a mixing point 11", in which sample and reagent are not introduced in parallel into the reaction channel but in succession by way of a change-over valve 37. As apparent from FIG. 6, very short segments of sample P and reagent R are positioned one behind the other within a block, sample P and reagent R following one another alternately. This creates a plurality of interfaces 36" through which the corresponding intermixing can be effected.

FIG. 7 shows a modified sample removing station 25'. One end of the sample duct 20 is immersed in a reservoir 38 for a fluid- for example, distilled water. Using the pump 24, the distilled water is sucked out of the reservoir 38. the sample duct 20 is connected to a mixing channel 39 which is bounded on one side by a membrane 40. On the other side of the membrane 40 there is a supply channel 41 which is in connection by way of a supply duct 42 with a reservoir of the substance or the fluid which is to be analyzed for a specific constituent. Pumping means, not illustrated, convey the fluid to be analyzed through the supply channel 41. As this is taking place, the constituent to be analyzed, to which the membrane 40 is matched, diffuses through the membrane 40 into the mixing channel 39. It is taken up by the fluid flowing through the mixing channel 39. The fluid supplemented with the constituent to be analyzed can then be fed by way of the change-over valve 7 or even directly into the sample line 10. In the latter case, analysis is effected continuously. The length of the individual samples can be regarded as infinitesimally small for the purposes of understanding operation. In that case, the volume ratio between sample and reagent fluids is kept constant not only over a block but over several blocks or even permanently.

The control unit 29 controls not only pumps 4 and 24 for carrier fluid and sample, but also pumps 14 and 15 for the reagents. To ensure synchronous operation of the pumps, all the pumps or their drives can be coupled back to the control unit 29, so that the control unit 29 is able to monitor the individual delivery volumes. One should note at this point that it is possible, of course, to use more than the two reagents described. In some cases it will also be sufficient to use just one reagent. The control device 29 is able to control the respective pumps synchronously with one another. The pumps are preferably in the form of piston pumps, which are driven either by a d.c. motor or a by stepper motor. In this manner, it is possible to achieve an extremely accurate setting of the delivery volumes of the respective pumps. The control device 29 drives the corresponding pumps 4, 25, 14, 15 in such a way that very accurately controlled fluid volumes enter the reaction channel 16. This has the advantage inter alia that in, fact a layering of sample and reagent can be achieved in the reaction channel 16.

The control device 29 can stop the pumps 14, 15 and 24 from time to time, and indeed for a relatively long period of time, and operate just the pump 4, so that the carrier fluid can be used to rinse out the apparatus 1.

FIG. 8 shows diagrammatically a representation of the new analysis method. Adjacent sample segments S D are introduced together with their associated reagent $R_n$ into the channel in such a manner that the mean local volume ratio between sample and reagent is constant. Numbering of the sample and reagent segments is not necessary per me, but makes "accounting" and subsequent explanation easier. The same reagent could, of course, be used for all samples.

Together with its reagent $R_n$, each sample $S_n$ forms a block B. At the instant at which it is introduced, the leading and trailing interfaces of the blocks B are aligned substantially evenly and orthogonally to the direction of flow. The volume ratio of samples $S_n$ and reagents $R_n$ are indicated beneath this initial alignment. The lowest line shows the ratio of reagent to total volume of sample and reagent.

At the end of the reaction channel 16, through which blocks B flow with a laminar flow, two changes have occurred compared with the state on feeding in. Firstly, the layers of sample and reagent can no longer be distinguished from one another. On the contrary, each sample has mixed with the reagent associated with it. Secondly, an axial dispersion has taken place between adjacent blocks, that is to say, the interfaces between adjacent blocks are no longer even and substantially orthogonal with respect to the direction of flow. On the contrary, the blocks have "bulged out" in the direction of flow at their leading end, as is known from laminar flow profiles, and have "caved in" in the direction of flow at their trailing end. It is important here, however, that the flow rate, and consequently the extent of the corresponding deformation of the blocks, is selected to be so low that in each block B there remains a core ("reaction core") b, which contains exclusively the respective sample $S_n$ with its associated reagent $R_n$. Only the reaction product that is of importance for the sample $S_n$ is therefore present in this core b.

The advantage of this arrangement is shown by the plot of the signal at the output of the detector 17 which is illustrated at the right-hand upper side of FIG. 8. The plot of this signal has separate plateaus which are stable over a definite period of time and are joined to one another by individual transitions. The plateaus can be evaluated with relatively little effort.

The volume ratios of sample and reagent are plotted beneath the "end portion" of the reaction channel 16. For the sake of simplicity, a linear change of sample or reagent is assumed in the transition regions between adjacent blocks. The variations from the actual conditions occurring here are negligible. Since the volume ratios of sample and reagent also change synchronously and uniformly in the transition segment between two adjacent blocks, the volume ratio between sample and its associated reagent remains constant also in these regions.

The detector, which always evaluates a certain volume of fluid at a time, that is, has an integral behaviour, will in this region detect both the reaction products of a sample $S_n$ with its reagent $R_n$ and the reaction products of an adjacent block, that is, the sample $S_n+1$ with reagent $R_n+1$. This creates the transient transitions between individual plateaus. But this has no influence on the fact that after such a transition a stable plateau is obtained again. Because of the low axial dispersion, attributable to the low flow rate, the individual blocks do not intermix completely. But within a block there is a very good intermixing, chiefly as a result of radial dispersion. The detector has an integrating effect, that is to say, the measuring signal reflects a kind of mean value over a detector volume. This detector volume is smaller than the volume of the reaction core. Although on the one hand this enables local disturbances to be evened-out, on the other hand the influence of adjacent samples on the measurement is avoided.

The low flow rate has the advantage that the reaction channel 16 can be made relatively short. The necessary reaction time is nevertheless achieved with the low flow rate.

By using blocks of sample and reagent that adjoin one another, the preceding sample-reagent mixture is washed out by the following one. This allows a significantly faster sequence of measurements of individual samples because the dilution caused by the known carrier fluid does not still have to be eliminated first.

In a first example, calcium is to be detected in water. Here, a solution of 8-hydroxyquinoline is used as the first reagent solution R1. A solution of ortho-cresolpthalein complexone is used as second reagent. Table 1 shows some results obtained during such an analysis of discrete calcium samples. The frequency with which samples were taken was 30 per hour. However, this frequency of analysis can, if necessary, be increased without problems. The flow rate was 90 µl/min. The length of the reaction channel 16 was 85 mm, and the cross-sectional area of the reaction channel 16 was 0.2 mm$^2$.

TABLE 1

| Time | Calcium (ppm present) | Calcium (ppm detected) |
|---|---|---|
| 8.15 | 1.00 | 1.01 |
| 8.17 | 5.00 | 4.98 |
| 8.19 | 1.00 | 1.01 |
| 8.21 | 5.00 | 4.97 |
| 8.23 | 2.50 | 2.49 |
| 8.25 | 5.00 | 4.98 |
| 8.27 | 2.50 | 2.50 |
| 8.29 | 3.90 | 3.92 |
| 8.31 | 1.00 | 1.00 |
| 8.33 | 3.90 | 3.89 |
| 8.35 | 2.50 | 2.51 |
| 8.37 | 5.00 | 4.99 |
| 8.39 | 3.90 | 3.91 |

Before the measurement, it is useful to undertake a calibration. For that purpose, analysis solutions that have exactly known concentrations are used. The treatment of the analysis solutions is effected exactly as for the sample solutions. All parts of the analysis system 1, including the carrier and reagent solutions, should preferably be kept at a constant predetermined temperature, in order to improve the accuracy and precision.

A second example shows results for a continuous analysis of nitrate in a sewage purification plant. Here, a construction according to FIG. 7 is used, that is to say, the take-up of nitrate into the sample solution is effected by means of dialysis. One should note that the construction according to FIG. 7 can be used not only in place of the sample removal station 25, but also in place of the change-over valve 7. The carrier fluid in this case flows past the membrane 40 in order to take up the nitrate. By controlling the pump 4 using the control unit 29, the dwell time of individual carrier fluid segments or blocks in front of the membrane 40 can be adjusted. The outside of the membrane can also be immersed directly in the sewage, so that the supply channel 41 and the supply duct 42 can be omitted. The analysis can then be effected continuously, that is to say, the carrier fluid flows past the membrane 40 continuously.

To analyze the nitrate, three reagent solutions were required, namely, hydrazine, sulphanilamide and N-(1-naphthyl)ethylene diamine. The pump 4 for the carrier fluid and the three pumps for the three reagents were operated continuously. The total flow rate was 60 µl/min. At specific intervals samples were taken and analyzed using the method known from DE 28 06 157 C2. In that method, however, cadmium was used instead of hydrazine f or the nitrate reduction.

TABLE 2

| Time | Nitrate (ppm) invention | Nitrate (ppm) DE 2806157 C2 |
|---|---|---|
| 16.13 | 0.8 | 0.6 |
| 16.21 | 1.3 | 1.1 |
| 16.26 | 1.7 | 1.5 |

TABLE 2-continued

| Time | Nitrate (ppm) invention | Nitrate (ppm) DE 2806157 C2 |
|---|---|---|
| 16.31 | 2.1 | 2.5 |
| 16.38 | 2.9 | 3.2 |
| 16.44 | 3.5 | 4.2 |
| 16.55 | 5.1 | 5.2 |
| 17.01 | 5.8 | 6.1 |
| 17.08 | 7.1 | 7.3 |
| 16.16 | 8.4 | 8.1 |
| 17.21 | 9.3 | 8.9 |
| 17.33 | 10.5 | 10.5 |

The average reaction time for the sample and the reagents is held constant in the system with a continuous operation of the system, which means that the chemical reaction is not necessarily fully concluded when the reaction product passes though the detector. In so w applications it may, however, be an advantage to operate the system not continuously but intermittently, so that a longer, but accurately controlled time is available for the chemical reaction. If, for example, the flow is interrupted when the mixture of sample and reagent has reached the detector, the chemical reaction can be monitored over a desired time or until a desired level is reached. A second reason for interrupting the continuous flow is that with accurately controlled waiting times a larger proportion of the constituent to be analyzed is able to pass through the membrane 40, if such a membrane is used.

Using the proposed method, the individual sample blocks are no longer separated by air bubbles or segments of carrier fluid. On the contrary, they adjoin each other without a gap. Sample and reagents are fed synchronously into a narrow reaction channel, and relatively accurately controlled individual flow rates are maintained. The shape and dimensions of the reaction channel 16 are of some significance. Since the cross-sectional area of the reaction channel 16 is less than 0.5 mm$^2$, and in particular less than 0.2 mm$^2$, and the length is less than 250 mm, and in particular less than 200 mm, very few chemicals are consumed. Furthermore, an elongate cross-sectional area is preferred to a round or square cross-sectional area, so that the interface between sample and reagent can be made as large as possible, which improves mutual intermixing. The overall flow rate can be kept below 100 µl/min, and in particular below 50 µl/min. Altogether, a Reynolds number of 5 or less can be achieved.

With the construction illustrated in FIG. 6, very accurate and predetermined volume percentages of sample and reagents can likewise be introduced into the reaction channel 16. In this case it is assumed that the addition of sample and reagent is effected periodically very accurately in order to keep the volume ratio constant. Each addition is intended to be very small in this case, so that the desired samplereagent ratio in the reaction channel 16 is achieved a short distance after the mixing point 11". The same forms and dimensions of the reaction channel 16 as those in the embodiments illustrated in FIG. 4 and 5 can be used here. In place of the change-over valve 37, the sample duct 10 and the reagent duct 12 can also be led directly into the reaction channel 16 if the pumps are operated alternately with the desired accuracy. This can be achieved relatively easily in particular if the pumps are driven by d.c. motors or stepper motors. The pumps that are responsible for pumping sample fluid and reagent fluid then alternately receive a pulse so that they feed the desired small amounts of sample fluid and reagent fluid correspondingly alternately into the reaction channel 16.

When such an analysis apparatus is used for sewage analysis in a purification plant, the amount of chemicals required can be reduced to such an extent that three liters per month is sufficient.

We claim:

1. An analysis apparatus comprising a sample feed duct, at least one reagent feed duct, a sample pump, at least one reagent pump, a reaction channel, a detector, and a controller for controlling the pumps to feed sample and reagent into the reaction channel as a block, wherein each pump has a delivery amount which is individually controllable and wherein the controller is operative to control the pumps to feed sample and reagent into the reaction channel alternatingly to form sample and reagent segments substantially shorter than the length of the block.

2. An analysis apparatus as in claim 1 wherein a local volume ratio between sample and reagent, averaged over a reaction channel section of predetermined length, is substantially constant along the length of the block.

3. An analysis apparatus as in claim 1 wherein each pump is a piston pump driven by a separate d.c. or stepper motor.

4. An analysis apparatus as in claim 1 wherein the detector has a detector volume which is smaller than the volume of a reaction core within the block.

* * * * *